(12) United States Patent
Norris et al.

(10) Patent No.: US 6,359,137 B1
(45) Date of Patent: Mar. 19, 2002

(54) PROCESS FOR PREPARING TROVAFLOXACIN ACID SALTS

(75) Inventors: Timothy Norris, Gales Ferry; Keith M. DeVries, Chester; Peter R. Rose, Ledyard, all of CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/383,320

(22) Filed: Aug. 26, 1999

Related U.S. Application Data

(60) Provisional application No. 60/098,944, filed on Sep. 3, 1998.

(51) Int. Cl.⁷ .................... C07D 471/04; C07D 209/52
(52) U.S. Cl. ........................ 546/123; 548/515
(58) Field of Search ........................ 546/123; 548/515

(56) References Cited

U.S. PATENT DOCUMENTS 6,184,380 B1 * 2/2001 Chiu et al. .................. 546/123

* cited by examiner

*Primary Examiner*—Bernard Dentz
(74) *Attorney, Agent, or Firm*—Peter Richardson; Paul Ginsburg; Bryan Zielinski

(57) ABSTRACT

Trovafloxacin acid salts are prepared via the hydrolysis of imine intermediates using mineral acid including, but not limited to, methanesulfonic acid, ethanesulfonic acid, benzenesulfonic acid, nitric acid, sulfuric acid, phosphoric acid, hydrochloric acid, hydrobromic acid, tartaric acid, citric acid, acetic acid, and maleic acid. Trovafloxacin acid salts are useful as antibiotic agents.

21 Claims, No Drawings

PROCESS FOR PREPARING TROVAFLOXACIN ACID SALTS

This application claims priority from Provisional Application 60/098,944 filed Sep. 3, 1998.

1. FIELD OF THE INVENTION

This invention relates to a process for preparing trovafloxacin acid salts. Trovafloxacin acid salts can be obtained from the hydrolysis of an imine intermediate using mild conditions.

2. BACKGROUND OF THE INVENTION

Quinolone and naphthyridone carboxylic acids, zwitterionic salts thereof, and pharmaceutically acceptable salts thereof, are useful as antibacterial agents, and have been prepared according to methods described in, e.g., U.S. Pat. No. 4,738,968 to Matsumoto et al., U.S. Pat. No. 4,382,937 to Matsumoto et al., U.S. Pat. No. 4,382,892 to Hayakawa et al., U.S. Pat. No. 4,571,396 to Hutt et al., U.S. Pat. No. 4,416,884 to Ishikawa et al., U.S. Pat. No. 4,775,668 to Jefson et al., U.S. Pat. No. 5,164,402 to Brighty and U.K Patent Publication No. 2,191,776 to Toyama Chemical Co. Ltd.

(1α,5α,6α)-7-(6-Amino-3-azabicyclo[3.1.0.]hex-3-yl)-1-(2,4-difluorophenyl)-6-fluoro-1,4-dihydro-4-oxo-1,8-naphthyridine-3-carboxylic acid, also known as trovafloxacin, is one type of naphthyridone carboxylic acid having preferred antibacterial properties.

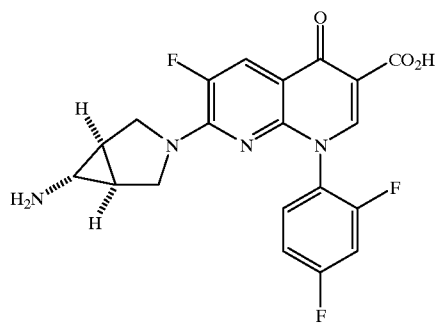

Like trovafloxacin, trovafloxacin acid salts possess antibacterial properties. Trovafloxacin acid salts are aqueous-soluble prodrug forms of trovafloxacin. Trovafloxacin hydrochloride has been previously obtained by coupling ethyl 7-chloro-1-(2,4-difluorophenyl)-6-fluoro-1,4-dihydro-4-oxo-1,8-naphthyridine-3-carboxylate:

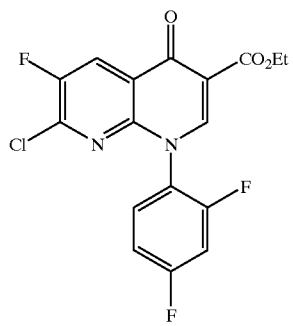

with [1α, 5α, 6α]-6-tert-butoxycarbonylamino-3-azabicyclo[3.1.0.]hexane:

and hydrolyzing the resulting product with aqueous hydrochloric acid (U.S. Pat. No. 5,164,402 to Brighty, Example 12A).

More recently, trovafloxacin methanesulfonate has been obtained by coupling ethyl 7-chloro-1-(2,4-difluorophenyl)-6-fluoro-1,4-dihydro-4-oxo-1,8-naphthyridine-3-carboxylate with [1α,5α,6α]-6-tert-butoxycarbonylamino-3-azabicyclo[3.1.0.]hexane, and hydrolyzing the resulting product with methanesulfonic acid (U.S. Pat. No. 5,763,454 to Handanyan et al.

While the above processes reliably provide usable quantities of trovafloxacin acid salts, the above processes also produce molar equivalents of isobutylene gas as a byproduct of hydrolysis of the tert-butoxycarbonyl protecting groups. Isobutylene is highly combustible, and is believed to exert a deleterious effect on the atmosphere's ozone layer. Accordingly, a process for obtaining trovafloxacin acid salts that does not result in the production of hazardous isobutylene gas would be highly desirable and advantageous.

Citation or identification of any reference in Section 2 of this application shall not be construed as an admission that such reference is available as prior art to the present application.

3. SUMMARY OF THE INVENTION

According to the invention, a process is provided for the preparation of a trovafloxacin acid salt having the formula (IV):

(IV)

wherein ZH is a mineral acid, comprising the step of contacting a compound of formula (I):

(I)

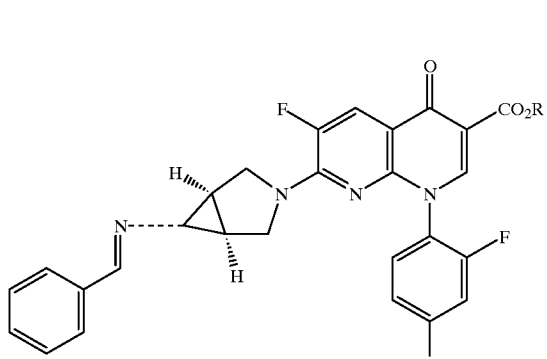

wherein R is a $C_1$–$C_6$ alkyl group; and the benzylidene ring of the compound of formula (I) is optionally substituted with one or more fluoro, chloro, bromo, iodo, C1–$C_6$ alkyl or C1–C6 alkoxyl groups, with a composition comprising the mineral acid ZH and water.

The invention further provides novel compounds of formula (I). The compounds of formula (I) are useful as intermediates for the synthesis of trovafloxacin acid salts. In a preferred embodiment of the invention, the compound of formula (I) is ethyl (1α,5α,6α)-7-(6-benzylidenylamino-3-azabicyclo[3.1.0]hex-3-yl)-1-(2,4-difluorophenyl)-6-fluoro-1,4-dihydro-4-oxo-1,8-naphthyridine-3-carboxylate:

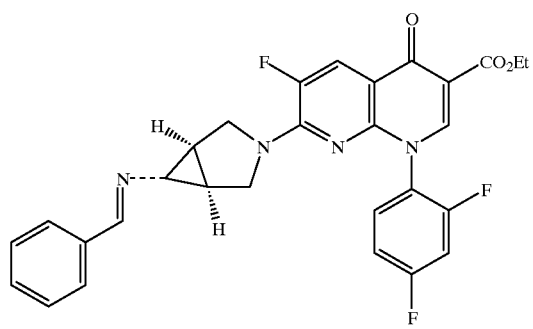

In addition, the invention provides a process for the preparation of a trovafloxacin acid salt having the formula (IV) comprising the steps of:

(a) contacting, in the presence of a tertiary amine base, a compound of formula (V):

(V)

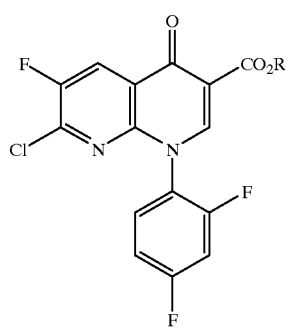

wherein R is defined above, with a compound of formula (II):

(II)

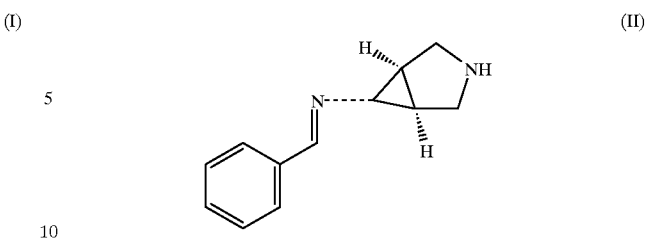

wherein the benzylidene ring of the compound of formula (II) is optionally substituted with one or more fluoro, chloro, bromo, iodo, $C_1$–$C_6$ alkyl or $C_1$–$C_6$ alkoxyl groups, to afford a compound of formula (I); and (b) contacting the compound of formula (I) with a composition comprising the mineral acid ZH and water.

The invention further provides novel compounds of the formula (II) useful as intermediates for the synthesis of compounds of formula (I) and trovafloxacin acid salts. In a preferred embodiment of the invention, the compound of formula (II) is (1α,5α,6α)-6-benzylidenylamino-3-azabicyclo[3.1.0]hexane:

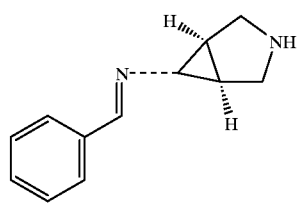

Still further, the invention provides a process for the preparation of trovafloxacin acid salts comprising the steps of:

(a) contacting, under substantially anhydrous conditions, a compound of formula (I) with the mineral acid ZH to afford a compound of formula (III):

(III)

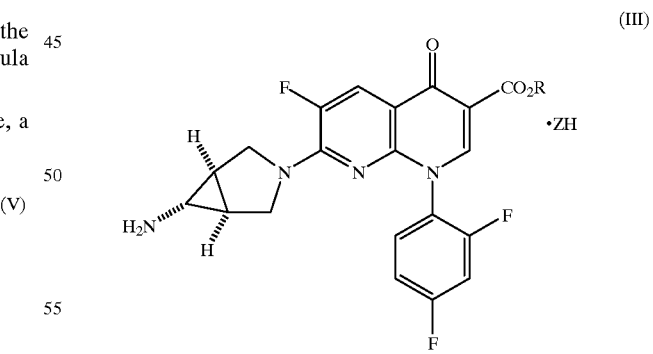

wherein R and ZH are defined above; and (b) contacting the compound of formula (III) with a composition comprising the mineral acid ZH and water.

The invention still further provides novel compounds of the formula (III) useful as intermediates for the synthesis of trovafloxacin acid salts. In a preferred embodiment of the invention, the compound of formula (III) is trovafloxacin ethyl ester methanesulfonate salt:

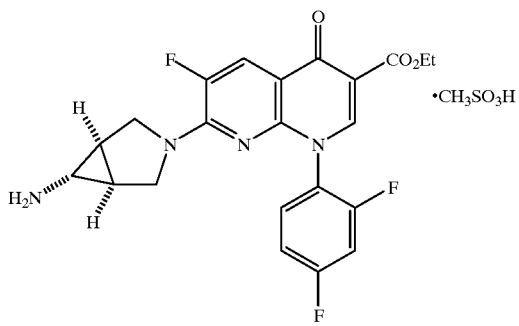

trovafloxacin ethyl ester methanesulfonate salt.

Since the compounds of formulae (I) and (II) are imines, they exist in either the syn or anti configuration. It is understood, that the invention as claimed includes either configuration or a mixture thereof.

4. DETAILED DESCRIPTION OF THE INVENTION

4.1 Definitions

The term "alkyl" as used herein includes a straight or branched chain hydrocarbyl group such as methyl, ethyl, propyl, iso-propyl, n-butyl, iso-butyl, sec-butyl, tert-butyl, etc.

The term "aryl" as used herein includes an aromatic hydrocarbyl group, such as phenyl or naphthyl, optionally substituted with 1 to 3 substituents independently selected from the group consisting of fluoro, chloro, cyano, nitro, trifluoromethyl, $(C_1-C_6)$alkoxy, $(C_6-C_{10})$aryloxy, trifluoromethoxy, difluoromethoxy and $(C_1-C_6)$alkyl.

The term "coupling reaction" as used herein means a reaction that results in the formation of a compound of formula (I) via reaction between a compound of formula (II) and a compound of formula (V) in the presence of tertiary amine base.

The term "hydrolysis reaction" as used herein means a reaction between a compound of formula (I), and a composition comprising mineral acid and water.

The term "imine-forming reaction" as used herein means the reaction of $(1\alpha,5\alpha,6\alpha)$-6-amino-3-azabicyclo[3.1.0]hexane with an optionally substituted aldehyde 5 as shown in Scheme 1.

The term "tertiary amine base" as used herein means an organic compound having a nitrogen atom forming three bonds, each of which being an $sp^2$ or $sp^3$ bond, solely with carbon atoms.

The term "trovafloxacin acid salt" as used herein means a mineral acid salt of trovafloxacin.

The term "substantially anhydrous conditions" as used herein means reaction conditions in which water is present in an amount no greater than about 1% by weight of the reaction mixture.

4.2 Compounds of Formula (II)

The compounds of formula (II) can be obtained according to Scheme 1. Nitrocyclopropanation of N-benzylmaleimide (1) affords $(1\alpha,5\alpha,6\alpha)$-3-N-benzyl-6-nitro-2,4-dioxo-3-azabicyclo[3.1.0]hexane (2). Reduction of the imino carbonyl groups of 2 with $NaBH_4$ in the presence of $BF_3$-THF provides $(1\alpha,5\alpha,6\alpha)$-3-N-benzyl-6-nitro-3-azabicyclo[3.1.0]hexane (3). Reduction of the nitro group of 3 to an amino group, with concomitant hydrogenolysis of its N-benzyl group, is accomplished via hydrogenation in the presence of 10% Pd on carbon to afford $(1\alpha,5\alpha,6\alpha)$-6-amino-3-azabicyclo[3.1.0]hexane (4). $(1\alpha,5\alpha,6\alpha)$-6-amino-3-azabicyclo[3.1.0]hexane is then reacted with an optionally substituted aldehyde 5 in an imine-forming reaction to afford a compound of formula (II) which bears an imino protecting group on the 6-amino group of $(1\alpha,5\alpha,6\alpha)$-6-amino-3-azabicyclo[3.1.0]hexane. Compounds 1–4 can be obtained using the methods described in Section 5, below, or can be obtained by methods known to those skilled in the art. Compound 3 can be obtained according to the methods of Braish et al., Synlett 1100 (1996). Aldehyde 5 is optionally substituted with one or more fluoro, chloro, bromo, iodo, $C_1-C_6$ alkyl or $C_1-C_6$ alkoxyl groups. Aldehydes 5 are commercially available, or readily synthesizable by means known to those skill in the art. Suitable aldehydes 5 include, but are not limited to, benzaldehyde, 2-chlorobenzaldehyde, 3-chlorobenzaldehyde, 4-chlorobenzaldehyde, 2-bromobenzaldehyde, 3-bromobenzaldehyde, 4-bromobenzaldehyde, 4-ethylbenzaldehyde, o-tolualdehyde, m-tolualdehyde, p-tolualdehyde and the like. Preferably, the aldehyde 5 is benzaldehyde.

Scheme 1

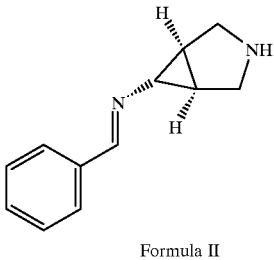

Formula II

The reaction that results in the formation of a compound of formula (II) (the imine-forming reaction) is performed by contacting (1α,5α,6α)-6-amino-3-azabicyclo[3.1.0]hexane (4) with an aldehyde 5. Generally the molar ratio of (1α,5α,6α)-6-amino-3-azabicyclo[3.1.0]hexane to the aldehyde 5 ranges from about 3:1 to about 1:3, preferably from about 1.5:1 to about 1:1.5, and most preferably from about 1.1:1 to about 1:1.1.

The imine-forming reaction can optionally be performed in the presence of an inert organic solvent. Suitable organic solvents include, but are not limited to, diethyl ether, tetrahydrofuran, methylene chloride, chloroform, carbon tetrachloride, toluene, xylenes, and simple alcohols, e.g., methanol and isopropanol. When the imine-forming reaction is performed in the presence of an inert organic solvent, the imine-forming reaction is performed as an about 1% to about 95% v/v solution in the inert organic solvent; preferably, as an about 5% to about 40% v/v solution in the inert organic solvent. Preferably, the imine-forming reaction is performed in the absence of an inert organic solvent.

The imine-forming reaction is preferably carried out in the presence of a tertiary amine base, regardless of whether or not an inert organic solvent is used. Without being bound to any particular theory, it is believed that the tertiary amine base functions by scavenging any trace amounts of acid, present in the reaction media, which can initiate decomposition of, e.g., hydrolyze, the compound of formula (II). Suitable tertiary amine bases include, but are not limited to, triethylamine, N,N-diisopropylethylamine, dimethylisopropylamine, methyldibutylamine, triphenylamine, pyridine, 4-dimethylaminopyridine, 2,6-lutidine, 2,4,6-collidine, N,N,N',N'-tetramethyl-1,8-naphthalenediamine, and the like. Preferably, where a tertiary amine base is used, the tertiary amine base is triethylamine. Where a tertiary amine base is used, it is preferably present in an amount in excess of (1α,5α,6α)-6-amino-3-azabicyclo[3.1.0]hexane or of an aldehyde 5, whichever is present in greater amount. More preferably, the molar ratio of tertiary amine base to (1α,5α,6α)-6-amino-3-azabicyclo[3.1.0]hexane or of an aldehyde 5, whichever is present in greater amount, is about 10:1 to about 2:1, most preferably from about 5:1 to about 2:1.

The imine-forming reaction is carried out at a temperature of about room temperature to about the reflux temperature of any inert organic solvent or tertiary amine base used, preferably at a temperature of about room temperature to about 120° C., more preferably at a temperature of about 45° C. to about 110° C., and most preferably at a temperature of about 70° C. to about 100° C.

When the imine-forming reaction is performed in the absence of an inert organic solvent, but in the presence of triethylamine tertiary amine base, the imine-forming reaction is carried out at about the reflux temperature of triethylamine.

The compounds of formula (II) obtained from the imine-forming reaction can be purified from their reaction mixture using standard recrystallization methods known to those skilled in the art, or can be obtained by merely concentrating the imine-forming reaction mixture, optionally in vacuo, to remove inert organic solvent or tertiary amine base. Alternatively, the compounds of formula (II) can be formed in situ, and used without purification as intermediates for obtaining compounds of formula (I) and trovafloxacin acid salts.

In a preferred embodiment of the invention, aldehyde 5 is benzaldehyde, and the compound of formula (II) is (1α,5α,6α)-6-benzylidenylamino-3-azabicyclo[3.1.0]hexane.

4.3 Compounds of Formula (I)

In general, compounds of formula (I) are obtained by combining, in no preferred order, a compound of formula (II), a compound of formula (V), and a tertiary amine base. Compounds of formula (II) can be obtained according to the methods described in Section 4.3, above. Compounds of formula (V) can be obtained according to the methods of U.K. Patent Publication No. GB 2,191,776.

The tertiary amine base is as described above for the imine-forming reaction. Preferably, the tertiary amine base has the formula $(R^2)(R^2)(R^2)N$, wherein each $R^2$ is independently a $C_1$–$C_6$ alkyl or $(C_6$–$C_{10})$aryl group; or the tertiary amine base is an aromatic compound having an endocyclic nitrogen atom. Suitable tertiary amine bases include, but are not limited to, triethylamine, N,N-diisopropylethylamine, dimethylisopropylamine, methyldibutylamine, triphenylamine, pyridine, 4-dimethylaminopyridine, 2,6-lutidine, 2,4,6-collidine, N,N,N',N'-tetramethyl-1,8-naphthalenediamine, and the like. Preferably, the tertiary amine base is triethylamine.

The molar ratio of the compound of formula (II) to the compound of formula (V) ranges from about 1.5:1, to about 1:1.5, and preferably from about 1.3:1 to about 1:1.3. The molar ratio of the tertiary amine base to the compound of formula (II) or to the compound of formula (V), whichever is used in the larger amount, is generally from about 10:1 to about 1:1, preferably from about 6:1 to about 1:1.

Without being bound to any particular theory, it is believed that the use of the tertiary amine base substantially avoids the formation of unwanted byproducts resulting from imine hydrolysis and subsequent reaction of the primary exocyclic amino group of a compound of formula (II) with the chloro group at the 7-carbon atom of the compound of formula (V). In addition, the tertiary amine base facilitates the bond forming process between the 7-carbon atom of the compound of formula (V) and the cyclic nitrogen atom of the compound of formula (II).

If the tertiary amine base sufficiently solubilizes the compound of formula (II) and the compound of formula (V), the coupling reaction need not be performed in the presence of additional solvent. However, under certain circumstances, it may be desired that the coupling reaction proceed in the presence of a coupling reaction solvent, e.g., to better solubilize reagents or to control reaction exothermicity. Suitable coupling reaction solvents include $(C_1$–$C_6)$ alcohols, such as methanol, ethanol and isopropanol; ethers, such as tetrahydrofuran (THF) and diethylether, polar aprotic solvents, such as dimethylsulfoxide, acetonitrile, dimethylformamide and N-methylpyrrolidinone; and mixtures thereof. The compound of formula (II) and the compound of formula (V) should be at least partially soluble in the coupling reaction solvent chosen; accordingly, it is well within the purview of one of skill in the art to select an appropriate solvent or mixture of solvents if necessary.

The coupling reaction is conveniently performed at a temperature of about 60° C. or above, and for a period of time ranging from about 1 hour to about 48 hours, preferably for a period of time ranging from about 2 hours to about 24 hours. More preferably, the coupling reaction is performed at the reflux temperature of the tertiary amine base or particular solvent used, and for a period of time ranging from about 6 hours to about 20 hours.

The product of the coupling reaction, i.e., a compound of formula (I), can be purified by recrystallization from common laboratory solvents, or by other methods known to those skilled in the art. Where the compound of formula (I) is insoluble in the tertiary amine base or in the coupling reaction solvent, the compound of formula (I) can be isolated by filtration, and optionally recrystallizing the compound of formula (I) from a common laboratory solvent, or mixtures thereof, or purifying the compound of formula (I) using any other method(s) known to those skilled in the art.

The compound of formula (II) used in the coupling reaction can be either isolated and purified from the imine-forming reaction described in Section 4.2, above, or preferably formed and contacted with a compound of formula (V) and the tertiary amine base in situ. In this regard, the compound of formula (II) is formed according to the imine-forming reaction described above, and to the imine-forming reaction mixture is added a compound of formula (V). If tertiary amine base is used in the imine-forming reaction, the addition of additional tertiary amine base to the coupling reaction is optional. If tertiary amine base is not present in a solution of a compound of formula (V), tertiary amine base is added to the coupling reaction either in conjunction with, or prior or subsequent to, addition of the compound of formula (V).

4.4 Trovafloxacin Acid Salts

Trovafloxacin acid salts are obtained by contacting a compound of formula (I) with a composition comprising mineral acid and water (the hydrolysis reaction). Without being bound to any particular theory, it is believed that the mineral acid removes the imino protecting group from the compound of formula (I), and that the composition comprising mineral acid and water hydrolyzes the ester group at the 3-carbon atom of the compound of formula (I) to form trovafloxacin which forms a stable acid salt with 1 equivalent of the mineral acid used in the hydrolysis reaction.

Suitable mineral acids include, but are not limited to, methanesulfonic acid, ethanesulfonic acid, benzenesulfonic acid, nitric acid, sulfuric acid, phosphoric acid, hydrochloric acid, hydrobromic acid, tartaric acid, citric acid, acetic acid, and maleic acid and the like. It will be understood that the trovafloxacin acid salt obtained from the hydrolysis reaction is a trovafloxacin salt of the particular mineral acid used therein.

In general, the molar ratio of mineral acid to the compound of formula (I) ranges from about 10:1 to about 1:1, preferably from about 5:1 to about 2:1. The weight ratio of water to the total weight of the compound of formula (I) and mineral acid is about 10:1 to about 2:1.

Optionally, a water soluble organic solvent can be added to the hydrolysis reaction in order to help solubilize the compound of formula (I). Such a water soluble organic solvent preferably is non-nucleophilic and does not form a carboxylic acid derivative with the ester group of the compound of formula (I), or with the carboxyl group of the trovafloxacin acid group, at its 3-carbon atom. Water soluble organic solvents useful in this regard include, but are not limited to, tetrahydrofuran, dimethylformamide, dimethylsulfoxide, N-methylpyrrolidinone, and the like. If a water soluble organic solvent is used in the hydrolysis reaction, the water soluble organic solvent is preferably tetrahydrofuran.

The hydrolysis reaction is performed at a temperature ranging from about room temperature to about the reflux temperature of water or of the water soluble organic solvent, for a period from about 1 hour to about 48 hours. Preferably, the hydrolysis reaction is performed at the reflux temperature of water or of the water soluble organic solvent, for a period from about 12 hours to about 36 hours.

The trovafloxacin acid salt can be isolated from the hydrolysis reaction by concentrating the hydrolysis reaction mixture to a reduced volume, optionally cooling the resulting concentrate, and filtering the resulting trovafloxacin acid salt precipitate. The hydrolysis reaction mixture may be pre-treated with decolorizing carbon, and filtered, prior to concentration. In addition, it may be desirable to manually or mechanically granulate the trovafloxacin acid salt product prior to filtration. The filtered trovafloxacin acid salt product can optionally be recrystallized using common laboratory solvents, or purified using other means known to those skilled in the art.

It is to be pointed out that trovafloxacin acid salts can be also obtained from a compound of formula (I) via a two-step process: in the first step, the imino protecting group is removed from the compound of formula (I) without hydrolysis of the ester group at its 3-carbon atom, and forms a compound of formula (III); and in the second step, the ester group at the 3-carbon atom of formula (III) is hydrolyzed to afford a trovafloxacin acid salt. Accordingly, compounds of formula (III) are useful as intermediates for the synthesis of, as well as prodrugs for, trovafloxacin acid salts.

Compounds of formula (III) are prepared by contacting a compound of formula (I) with a mineral acid, optionally in the presence of an inert organic solvent. Generally, the molar ratio of mineral acid to the compound of formula (I) ranges from about 10:1 to about 1:1, preferably from about 5:1 to about 2:1. The inert organic solvent may be added to help solubilize the compound of formula (I). If an inert organic solvent is added, the inert organic solvent is preferably tetrahydrofuran.

It will be understood that because the compounds of formula (III) retain an ester group at the 3-carbon atom position, the reaction used to form compounds of formula (III) is performed under substantially anhydrous conditions so as to exclude water which can hydrolyze the ester group.

The reaction used to obtain compounds of formula (III) is performed at a temperature ranging from about room temperature to about 80° C., for a period from about 1 hour to about 24 hours. Preferably, this reaction is performed at a temperature of about 40° C. to about 60° C., for a period from about 5 hours to about 20 hours.

The resulting compound of formula (III) can be isolated by cooling the reaction mixture to room temperature or below, and filtering the compound of formula (III) product. If it is desired that the compound of formula (III) be isolated in the form of a powder, the compound of formula (III) can be mechanically or manually granulated prior to filtration. Once filtered, the compound of formula (III) can be recrystallized, or purified using other means known to those skilled in the art.

Once the compound of formula (III) is isolated, the compound of formula (III) can be converted to a trovafloxacin acid salt by contacting the compound of formula (III) with a composition comprising mineral acid and water. Generally, the molar ratio of mineral acid to the compound of formula (III) ranges from about 5:1 to about 1:1, preferably from about 3:1 to about 1:1. The weight ratio of water to the total weight of the compound of formula (I) and mineral acid is about 10:1 to about 2:1.

Optionally, a water soluble organic solvent described above can be added to help solubilize the compound of formula (III). If a water soluble organic solvent is used, the water soluble organic solvent is preferably tetrahydrofuran.

The conversion of compounds of formula (III) to trovafloxacin acid salts takes place at a temperature ranging from about room temperature to about the reflux temperature of water or of the water soluble organic solvent, for a period from about 1 hour to about 12 hours. Preferably, this reaction is performed at a temperature of about 50° C. to about 100° C., for a period from about 4 hours to 8 hours.

The trovafloxacin acid salt so obtained can be isolated according to the methods of the hydrolysis reaction described above.

4.5 Trovafloxacin Zwitterion

While trovafloxacin acid salts are useful as antibacterial agents, it may be desirable to formulate the trovafloxacin acid salts in a form having a higher weight percentage of active compound, i.e., in the absence of the acid salt In such a case, trovafloxacin acid salts obtained according to the methods described herein can be treated with saturated aqueous sodium bicarbonate (see International Publication No. WO 97/07800, Example 1A) to form trovafloxacin zwitterion having the structure below:

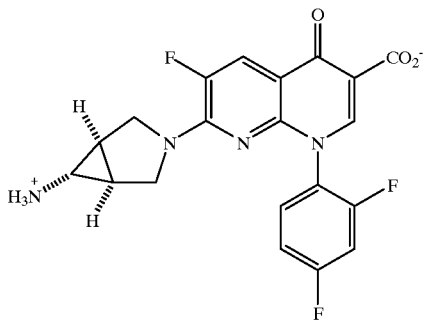

4.6 Methods for Using Trovafloxacin Acid Salts

Trovafloxacin acid salts are useful for the treatment of bacterial infections of broad spectrum, particularly the treatment of gram-positive bacterial strains.

Trovafloxacin acid salts may be administered alone, but will generally be administered in admixture with a pharmaceutical carrier selected with regard to the intended route of administration and standard pharmaceutical practice. For example, they can be administered orally or in the form of tablets containing such excipients as starch or lactose, or in capsules either alone or in admixture with excipients, or in the form of elixirs or suspensions containing flavoring or coloring agents. In the case of animals, they are advantageously contained in an animal feed or drinking water in a concentration of 5–5000 ppm, preferably 25–500 ppm. They can be injected parenterally, for example, intramuscularly, intravenously or subcutaneously. For parenteral administration, they are best used in the form of a sterile aqueous solution which can contain other solutes, for example, enough salt or glucose to make the solution isotonic. In the case of animals, the trovafloxacin acid salts can be administered intramuscularly or subcutaneously at dosage levels of about 0.1–50 mg/kg/day, advantageously 0.2–10 mg/kg/day given in a single daily dose or up to 3 divided doses.

The trovafloxacin acid salts can be administered to humans for the treatment of bacterial diseases by either the oral or parenteral routes, and may be administered orally at dosage levels of about 0.1 to 500 mg/kg/day, advantageously 0.5–50 mg/kg/day given in a single dose or up to 3 divided doses. For intramuscular or intravenous administration, dosage levels are about 0.1–200 mg/kg/day, advantageously 0.5–50 mg/kg/day. While intramuscular administration may be a single dose or up to 3 divided doses, intravenous administration can include a continuous drip. Variations will necessarily occur depending on the weight and condition of the subject being treated and the particular route of administration chosen as will be known to those skilled in the art.

The antibacterial activity of the trovafloxacin acid salts is shown by testing according to the Steer's replicator technique which is a standard in vitro bacterial testing method described by E. Steers et al., Antibiotics and Chemotherapy, 9, 307 (1959).

The following examples are set forth to assist in understanding the invention and should not be construed as limiting the invention described and claimed herein. Such variations of the inventions which would be within the purview of those in the art, including the substitution of all equivalents now known or later developed, are to be considered to fall within the scope of the invention incorporated herein.

EXAMPLE 1

(1α,5α,6α)-3-N-benzyl-6-nitro-2,4-dioxo-3-azabicyclo[3.1.0]hexane (2)

N-Benzylmaleimide (1) (500 g, 2.67 mole), 90% bromonitromethane (831 g, 5.34 mole), powdered molecular sieves, 200 mesh (2020 g) and toluene (12 dm$^3$) were stirred under nitrogen at −10° C. 1,2-dimethyl-1,4,5,6-tetrahydropyrimidine (616 g, 5.49 mole) was added slowly over about 3 hours maintaining the reaction temperature at <−8° C. throughout the addition. After completion of the addition, the reaction mixture was stirred for 1.5 h at 25° C., filtered under a nitrogen atmosphere in a sealed pressure filter to remove sieves and resulting tar, and the sieves were washed with toluene (2 L). The combined filtrates were washed with 2N dilute hydrochloric acid (3×750 cm$^3$), treated with carbon (50 g) at 70° C., 1 h filtered, concentrated, and triturated with 2-propanol (~4 dm$^3$) to obtain crystals of the above-titled compound (223 g, 34%) mp 116–118° C.; (Found: C, 58.2; H, 4.1; N, 11.3. $C_{12}H_{10}N_2O_4$ requires C, 58.5; H, 4.1; N, 11.4%); m/z 246 (M+), 200 (M+ —NO$_2$, 100%); δH (300 MHz; CDCl$_3$) 7.3 (m, 5H, Ph), 4.54 (s, 2H, benzylic), 4.45 (s, 1H, 6b), 3.35 (s, 2H, 3-ring).

EXAMPLE 2

(1α,5α,6α)-3-N-benzyl-6-nitro-3-azabicyclo[3.1.0]hexane (3)

Tetrahydrofuran (350 cm$^3$), sodium borohydride (14.1 g) and (1α,5α,6α)-3-N-benzyl-6-nitro-2,4-dioxo-3-azabicyclo[3.1.0]hexane (2) (35.0 g, mmol) obtained above were stirred under nitrogen for 0.25 h and then treated dropwise with boron trifluoride THF complex containing 21.5% $BF_3$ (44.9 cm$^3$) so that the exotherm was controlled to <40° C. After addition was completed, the reaction mixture was stirred for 3 h at 40° C., quenched slowly with water/THF 1:1 (70 cm$^3$) to avoid excessive foaming, and stirred for 0.5 h at 50° C. to ensure that the quench of unreacted diborane generated in situ was completed. The quench formed a salt slurry which was filtered and washed with THF (140 cm$_3$); the combined filtrate was partially concentrated, diluted with water (350 cm$^3$) and further concentrated to remove most of the THF, and extracted with ethyl acetate (140 cm$^3$). The resulting ethyl acetate solution was concentrated to afford the above-titled compound as a clear oil (30.6 g, 97%). Elemental analysis obtained from its mesylate salt, which was prepared by mixing an equivalent of (1α,5α,6α)-3-N-benzyl-6-nitro-3-azabicyclo[3.1.0] hexane with an equivalent of methanesulfonic acid in alcoholic solvent, and concentrating the resulting mixture (Found: C, 49.8; H, 6.0; N, 9.1; S, 10.2. $C_{12}H_{14}N_2O_2 \cdot CH_4O_3S$ requires C, 49.7; H, 5.8; N, 8.9; S, 10.2%); m/z 218 (M+); δH (300 MHz; CDCl$_3$) 7.3 (m, 5H, Ph), 4.63 (s, 1H, 6b), 3.6 (s, 2H, benzylic), 3.14 (d, 2H, 5-ring), 2.51 (m, 2H, 3-ring).

EXAMPLE 3

(1α,5α,6α)-6-amino-3-azabicyclo[3.1.0]hexane (4)

(1α,5α,6α)-3-N-Benzyl-6-nitro-3-azabicyclo[3.1.0] hexane (3) (25.2 g, 115.5 mmol), 10% Pd on carbon, 55% water content (10.0 g), water (125 cm$^3$) and 2-propanol (250 cm$^3$), were hydrogenated in a Parr apparatus at 50° C., 3.5 atm., 24 hr. The catalyst was filtered off, and the resulting filtrate was concentrated in vacuo to obtain the above-titled compound as an oil (10.4 g, 91.7%), purity GC 83%. The material so obtained was usable without further purification. Purification by column chromatography on silica gel using CHCl$_3$, 55%; CH$_3$OH, 35%; and concentrated NH$_4$OH, 10% yielded the above-titled compound as a clear oil; m/z 96 (M$^+$−2); δH (300 MHz, CD$_3$OD) 4.86 (s, NHs and MeOH), 2.97 (2H, d, J=11.4 Hz), 2.77 (2H, dt, J=1.4 and 11.4 Hz), 2.06 (1H, t, J=2.2 Hz), 1.42 (2H, td, J=1.4 and 2.2 Hz); δC (75.5 MHz, CD$_3$OD) 48.9, 32.5, 27.5.

EXAMPLE 4

Ethyl (1α,5α,6α)-7-(6-benzylidenylamino-3-azabicyclo[3.1.0]hex-3yl)-1-(2,4-difluorophenyl)-6-fluoro-1,4-dihydro-4-oxo-1,8-naphthyridine-3-carboxylate (1α,5α,6α)-3-N-Benzyl-6-nitro-3-azabicyclo[3.1.0] hexane (3) (30.9 g, 142 mmol) obtained above, 2-propanol (310 cm$^3$), water (30 cm$^3$), and 10% Pd on carbon, 50% water content (12.3 g) were hydrogenated at 50 psi and 50° C. for 18–24 hr in a Parr shaker. The Pd catalyst was filtered off, and the resulting pale yellow filtrate was azeotropically distilled at constant volume to remove water. The resulting solution was treated with triethylamine (46 g, 456 mmol) and heated to reflux. Benzaldehyde (15.0 g, 141 mmol) was added dropwise over 15 minutes. The reaction mixture was heated at reflux for 4 hr to form (1α,5α,6α)-6-benzylidenylamino-3-azabicyclo[3.1.0]hexane in situ. The resulting orange solution was cooled to 40–50° C., and ethyl 7-chloro-1-(2,4-difluorophenyl)-6-fluoro-1,4-dihydro-4-oxo-1,8-naphthyridine-3-carboxylic acid (42.45 g, 111 mmol; see United Kingdom Patent Publication No. GB 2,191,776) and triethylamine (13.1 g, 130 mmol) were added. The resulting slurry was heated at reflux for 16–18 h., cooled to 20° C. and stirred for 5 h. The slurry was filtered, and the above-titled compound was isolated as a white solid (75.5% yield based on (1α,5α,6α)-3-N-benzyl-6-nitro-2,4-dioxo-3-azabicyclo[3.1.0]hexane; 96.6% based on ethyl 7-chloro-1 -(2,4-difluorophenyl)-6-fluoro-1,4-dihydro-4-oxo-1,8-naphthyridine-3-carboxylic acid). The above-titled compound was recrystallized from acetonitrile, mp 148–155° C. decomp. (Found: C, 63.5; H, 4.4; F, 10.35; N, 10.7. $C_{29}H_{23}F_3N_4O_3 \cdot H_2O$ requires C, 63.3; H, 4.6; F, 10.35; N, 10.2%); m/z 533 (M$^+$+1); δH (300 MHz, CDCl$_3$) 8.33 (s, 1H), 8.29 (s, 1H), 7.97 (d, J=7.1 Hz, 1H), 7.58–7.61 (m, 2H), 7.46 (td, J=5.77, 8.6 Hz, 1H), 7.31–7.35 (m, 3H), 6.97–7.08 (m, 2H), 4.31 (q, J=7.1 Hz, 2H), 3.80 (br. s, 2H), 3.64 (br. s, 2H), 2.75 (t, J=1.8 Hz, 1H), 2.13 (s, 2H), 1.32 (t, J=7.1 Hz, 3H); $\nu_{max}$ (KBr) cm$^{-1}$ 1730, 1697, 1632.

EXAMPLE 5

Trovafloxacin Methanesulfonate Salt (Method A)

Tetrahydrofuran (250 cm$^3$), ethyl (1α,5α,6α)-7-(6-benzylidenylamino-3-azabicyclo[3.1.0]hex-3-yl)-1-(2,4-difluorophenyl)-6-fluoro-1,4-dihydro-4-oxo-1,8-naphthyridine-3-carboxylate (25.05 g, 47 mmol) obtained above, and water (250 cm$^3$) were treated with 97% methanesulfonic acid (13.3 g, 138 mmol) and heated to reflux for 24 h. The resulting solution was cooled to 45° C., treated with activated carbon (2.5 g) for 1 hr and filtered. The resulting filtrate was concentrated under vacuum to approximately 25% of its original volume to provide a white crystal slurry, cooled to 15–25° C., granulated for 4 h and filtered to yield the above-titled compound (16.86 g, 70.0%). mp 253–256° C. decomp.; (Found: C, 49.3; H, 3.75; F, 11.2; N, 11.0; S, 6.3. $C_{20}H_{15}F_3N_4O_3 \cdot CH_4O_3S$ requires C, 49.2; H, 3.7; F, 11.1; N, 10.9; S, 6.3%); δH (300 MHz; d$_6$-DMSO) 8.85 (s, 1H), 8.17 (br. m, 2H), 8.11 (d, 1H), 7.83 (m, 2H), 7.62 (m, 2H), 7.37 (m, 2H), 3.67 (br. s, 3H), 2.45 (s, 1H), 2.37 (s, 3H), 2.08 (s, 2H). The above-titled compound can also be isolated as a monohydrate.

EXAMPLE 6

Trovafloxacin Zwitterion

Tetrahydrofuran (250 cm$^3$), ethyl (1α,5α,6α)-7-(6-benzylidenylamino-3-azabicyclo[3.1.0]hex-3-yl)-1-(2,4-difluorophenyl)-6-fluoro-1,4-dihydro-4-oxo-1,8-naphthyridine-3-carboxylate (25.05 g, 47 mmol) obtained above, and water (250 cm$^3$) were treated with 97% methanesulfonic acid (13.3 g, 138 mmol) and heated to reflux for 24 h. The resulting solution, which contained trovafloxacin methanesulfonate salt, was cooled to 45° C., treated with activated carbon (2.5 g) for 1 hr and filtered. Treatment of the filtrate with saturated aqueous sodium bicarbonate to pH 8 (see PCT Publication No. WO 97/07800, example 1A) yields the above-titled compound.

EXAMPLE 7

Trovafloxacin Ethyl Ester Methanesulfonate Salt

Ethyl (1α,5α,6α)-7-(6-benzylidenylamino-3-azabicyclo [3.1.0]hex-3-yl)-1-(2,4-difluorophenyl)-6-fluoro-1,4-dihydro-4-oxo-1,8-naphthyridine-3-carboxylate (6.02 g, 11.3 mmol) obtained above, tetrahydrofuran (90 cm$^3$) and methanesulfonic acid (1.11 g, 11.2 mmol) were mixed together to form a slurry. The slurry was heated to 45–55° C., and held in this temperature range for 4 hours, at which time additional methanesulfonic acid (2.2g, 22.4 mmol) was added to the reaction mixture. After heating for an additional 12 hours in the temperature range 45–55° C., the reaction was completed. The reaction mixture was cooled to 0–25° C., granulated for up to 10 hours, filtered and dried under vacuum at 40–45° C. to afford the above-titled compound as a white solid (Yield 3.76 g, 62%).

EXAMPLE 8

Trovafloxacin Methanesulfonate Salt (Method B)

Trovafloxacin ethyl ester methanesulfonate salt (50.0 g, 92.5 mmol) obtained above was treated with tetrahydrofuran (450 cm$^3$), water (50 cm$^3$) and methanesulfonic acid (13.4 g, 139 mmol) to form a slurry. The reaction mixture slurry was heated at for 4 hours at 70–80° C., then 250 cm$^3$ of solvent was removed by distillation. The resulting concentrated reaction mixture was diluted with water (250 cm$^3$) to form a solution, which was heated at 70–80° C. for 2 hours until the reaction was completed. The remaining solvent (200 cm$^3$) was removed under vacuum at 55–65° C. The resulting residue was granulated at 20–25° C. for 16 hours, filtered and dried under vacuum at 30–50° C. to afford the above-titled compound (Yield: 43.8 g, (92.4%)). The above-titled compound was identical, in all material aspects, to trovafloxacin mesylate obtained in Example 5, above.

A number of references have been cited, the entire disclosures of which are incorporated herein by reference.

What is claimed is:

1. A process for preparing a trovafloxacin acid salt having the formula (IV):

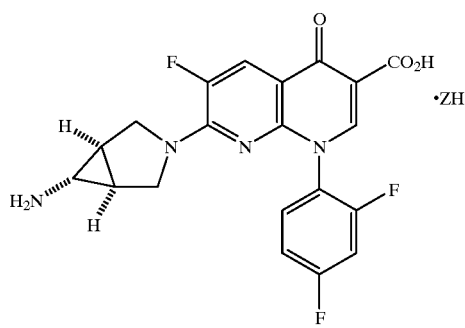

(IV)

wherein ZH is a mineral acid, comprising the step of contacting a compound of formula (I):

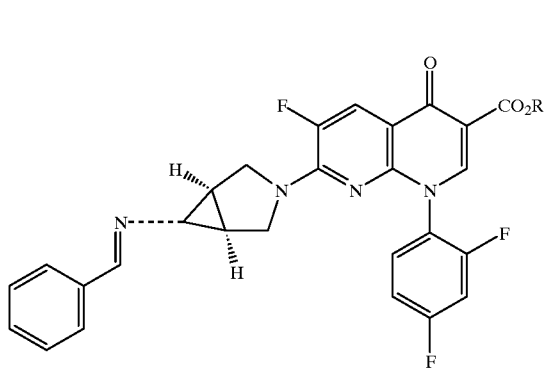

(I)

wherein R is a $C_1$–$C_6$ alkyl group; and
wherein the benzylidene ring of the compound of formula (I) is optionally substituted with one or more fluoro, chloro, bromo, iodo, $C_1$–$C_6$ alkyl or $C_1$–$C_6$ alkoxyl groups, with a composition comprising the mineral acid ZH and water.

2. The process of claim 1, wherein R is ethyl.

3. The process of claim 1, wherein the mineral acid is selected from the group consisting of methanesulfonic acid, ethanesulfonic acid, benzenesulfonic acid, nitric acid, sulfuric acid, phosphoric acid, hydrochloric acid, hydrobromic acid, tartaric acid, citric acid, acetic acid, and maleic acid.

4. The process of claim 1, wherein the process is performed in the presence of an inert organic solvent.

5. A process for preparing a trovafloxacin acid salt having the formula (IV):

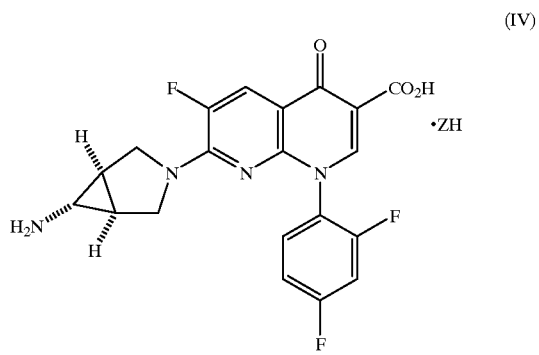

(IV)

wherein ZH is a mineral acid, comprising the steps of:

(a) contacting, in the presence of a tertiary amine base, a compound of formula (V):

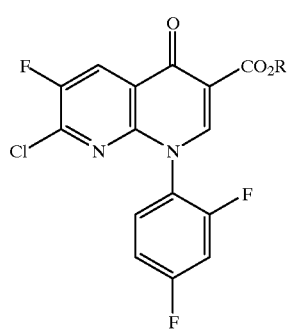

(V)

wherein R is a $C_1$–$C_6$ alkyl group, with a compound of formula (II):

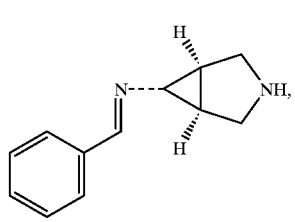

(II)

wherein the benzylidene ring of the compound of formula (II) is optionally substituted with one or more fluoro, chloro, bromo, iodo, $C_1$–$C_6$ alkyl or $C_1$–$C_6$ alkoxyl groups, to afford a compound of formula (I):

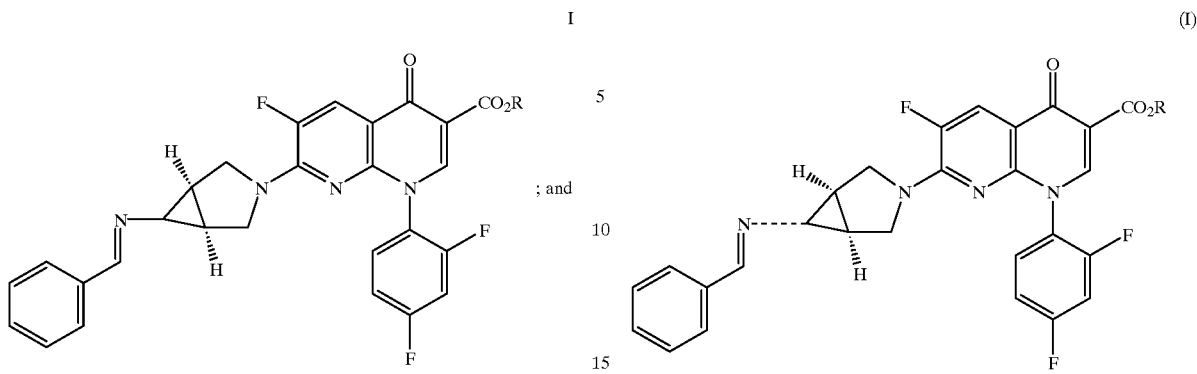

(b) contacting the compound of formula (I) with a composition comprising the mineral acid ZH and water.

6. The process of claim 5, wherein R is ethyl.

7. The process of claim 5, wherein the mineral acid is selected from the group consisting of methanesulfonic acid, ethanesulfonic acid, benzenesulfonic acid, nitric acid, sulfuric acid, phosphoric acid, hydrochloric acid, hydrobromic acid, tartaric acid, citric acid, acetic acid, and maleic acid.

8. The process of claim 5, wherein the tertiary amine base is selected from the group consisting of triethylamine, N,N-diisopropylethylamine, dimethylisopropylamine, methyldibutylamine, triphenylamine, pyridine, 4-dimethylaminopyridine, 2,6-lutidine, 2,4,6-collidine and N,N,N',N'-tetramethyl-1,8-naphthalenediamine.

9. The process of claim 6, wherein step (a) of the process is performed in the presence of an inert organic solvent.

10. The process of claim 6, wherein step (b) of the process is performed in the presence of a water soluble organic solvent.

11. A process for preparing a trovafloxacin acid salt having the formula (IV):

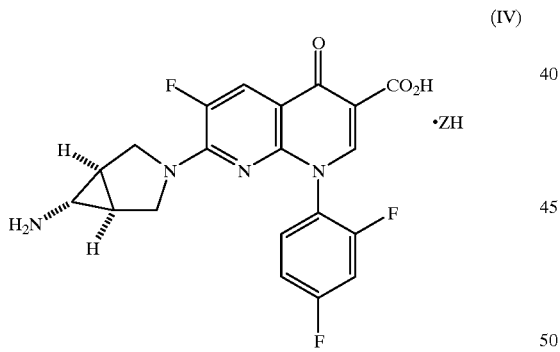

wherein ZH is a mineral acid, comprising the steps of:
(a) contacting, under substantially anhydrous conditions, a compound of formula (I):

wherein R is a $C_1$–$C_6$ alkyl group; and the benzylidene ring of the compound of formula (I) is optionally substituted with one or more fluoro, chloro, bromo, iodo, $C_1$–$C_6$ alkyl or $C_1$–$C_6$ alkoxyl groups, with mineral acid to afford a compound of formula (III):

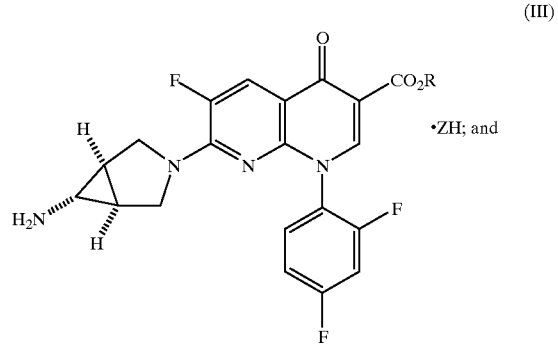

(b) contacting the compound of formula (III) with a composition comprising the mineral acid ZH and water.

12. The process of claim 11, wherein R is ethyl.

13. The process of claim 11, wherein the mineral acid is selected from the group consisting of methanesulfonic acid, ethanesulfonic acid, benzenesulfonic acid, nitric acid, sulfuric acid, phosphoric acid, hydrochloric acid, hydrobromic acid, tartaric acid, citric acid, acetic acid, and maleic acid.

14. The process of claim 11, wherein step (a) of the process is performed in the presence of an inert organic solvent.

15. The process of claim 11, wherein step (b) of the process is performed in the presence of a water soluble organic solvent.

16. A compound of formula (I):

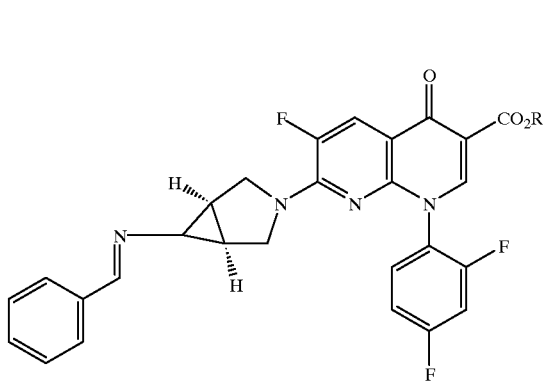

wherein R is a $C_1$–$C_6$ alkyl group; and the benzylidene ring of the compound of formula (I) is optionally substituted with one or more fluoro, chloro, bromo, iodo, $C_1$–$C_6$ alkyl or $C_1$–$C_6$ alkoxyl groups.

17. The compound of claim 16, wherein R is ethyl.

18. The compound of claim 16, wherein the compound is ethyl (1α,5α,6α)-7-(6-benzylidenylamino-3-azabicyclo[3.1.0]hex-3-yl)-1-(2,4-difluorophenyl)-6-fluoro-1,4-dihydro-4-oxo-1,8-naphthyridine-3-carboxylate.

19. A compound of formula (II):

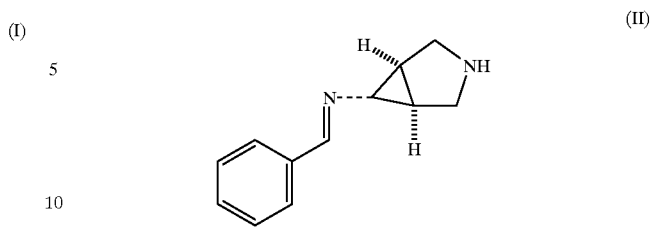

wherein the benzylidene ring of the compound of formula (II) is optionally substituted with one or more fluoro, chloro, bromo, iodo, $C_1$–$C_6$ alkyl or $C_1$–$C_6$ alkoxyl groups.

20. The compound of claim 19, wherein the compound is (1α,5α,6α)-6-benzylidenylamino-3-azabicyclo[3.1.0]hexane.

21. A compound of formula (III):

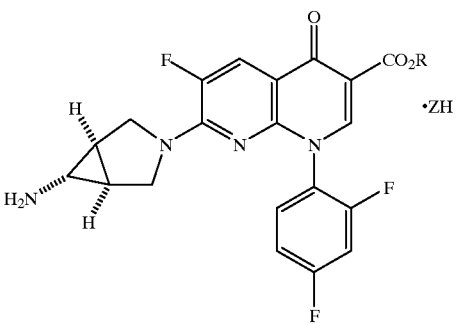

wherein R is a $C_1$–$C_6$ alkyl group, and ZH is a mineral acid.

* * * * *